United States Patent [19]

Lovrecich

[11] Patent Number: 5,569,469
[45] Date of Patent: *Oct. 29, 1996

[54] POORLY SOLUBLE MEDICAMENTS SUPPORTED ON POLYMER SUBSTANCES IN A FORM SUITABLE FOR INCREASING THEIR DISSOLVING RATE

[75] Inventor: Mara L. Lovrecich, Trieste, Italy

[73] Assignee: Vectorpharma International, S.p.A., Trieste, Italy

[ * ] Notice: The term of this patent shall not extend beyond the expiration date of Pat. No. 5,354,560.

[21] Appl. No.: 28,214

[22] Filed: Mar. 9, 1993

Related U.S. Application Data

[62] Division of Ser. No. 952,474, Sep. 28, 1992, Pat. No. 5,225,192, which is a continuation of Ser. No. 421,943, Oct. 16, 1984, abandoned.

[51] Int. Cl.$^6$ .............. A61K 9/50; A61K 9/22; A61K 9/70; B05D 3/04
[52] U.S. Cl. .............. 424/501; 424/78.02; 424/449; 424/457; 424/468; 424/499; 427/335; 427/336
[58] Field of Search .............. 424/78.02, 457, 424/468, 449, 499, 500, 501; 427/3, 335, 336

[56] References Cited

U.S. PATENT DOCUMENTS

| | | |
|---|---|---|
| 282,209 | 8/1981 | Tucker . |
| 303,642 | 12/1981 | Kangas . |
| 312,855 | 1/1982 | Grand . |
| 818,517 | 4/1989 | Kwee et al. . |
| 4,837,031 | 6/1989 | Denton .............. 424/464 |
| 4,882,167 | 11/1989 | Jang .............. 424/46 |
| 5,354,560 | 10/1994 | Lovrecich .............. 424/489 |
| 5,449,521 | 9/1995 | Lovrecich .............. 424/489 |

*Primary Examiner*—Carlos Azpuru
*Attorney, Agent, or Firm*—Birch, Stewart, Kolasch & Birch LLP

[57] ABSTRACT

A poorly soluble medicament is incorporated into particles of a crosslinked polymer which is swellable in water but insoluble in water, and the product obtained is brought into contact with a solvent able to swell the polymer. The product obtained by this treatment, and after being dried under vacuum, has a medicament dissolving rate which is considerably higher than that of the pure medicament.

5 Claims, No Drawings

POORLY SOLUBLE MEDICAMENTS SUPPORTED ON POLYMER SUBSTANCES IN A FORM SUITABLE FOR INCREASING THEIR DISSOLVING RATE

This application is a divisional of application Ser. No. 07/952,474, filed on Sep. 28, 1992; now U.S. Pat. No. 5,225,192, which was a continuation of Ser. No. 07/421,943, filed on Oct. 16, 1989, now abandoned; the entire contents of which are hereby incorporated by reference.

FIELD OF THE INVENTION

This invention relates to poorly soluble medicaments supported on polymer substances.

PRIOR ART

In numerous cases, orally administered medicaments are poorly adsorbed with the result that their hematic concentration is low and varies between subjects. These problems are very often due to poor water-solubility and wettability of the medicament. Various treatments have been used to overcome these problems, such as micronization and addition of surfactants, but the improvement is often very limited.

To improve the dissolution of poorly soluble medicaments it has recently been proposed to support said medicaments in crosslinked polymers which are swellable but not soluble in water.

B. Lippold et al. (D.O.S. 26 34 004) have patented a process which consists of incorporating medicament solutions into said polymers and drying the product obtained. An increase in dissolving rate has been found for diphenylhydantoin, tolbutamide and griseofulvin.

D.O.S. patent 33 20 583 describes incorporating sulphonylurea derivatives in water-insoluble supports, such as crospovidone (crosslinked polyvinylpyrrolidone) using solutions containing water-soluble polymers such as linear polyvinylpyrrolidone. This process also results in an increase in the medicament dissolving rate.

EP patent application 78 430 relates to dihydropyridine derivatives adsorbed on crospovidone together with polyvinylpyrrolidone, these demonstrating very fast absorption. SA patent application 87/0738 describes incorporating dihydropyridine/crospovidone adsorbates in a water-gellable polymer or mixture of polymers, to obtain improved release and absorption.

A considerable increase in hematic level has been obtained by administering medroxyprogesterone acetate incorporated in crospovidone (G.B. patent application 840, 3360). Other processes have also been proposed for incorporation into said water-insoluble polymers.

For example, G.B. patent 2,153,676 describes a co-heating method by which a mixture of an insoluble polymer and a medicament is heated to the medicament melting point with consequent incorporation of the molten medicament in the polymer lattice.

G.B. patent 2,153,678 relates to a co-grinding process by which a mixture of insoluble polymers and a medicament is ground in high-energy mill to produce improvement in the medicament dissolving characteristics deriving from incorporating the medicament molecules in the polymer.

SUMMARY

We have now found that the dissolving rate of poorly soluble medicaments can be considerably increased by a method characterised by:

1) incorporating the medicament into particles of a water-swellable but insoluble crosslinked polymer;
2) bringing the product obtained in stage 1) into contact with a solvent, in gaseous or liquid form, which is able to swell the polymer;
3) drying the product obtained in stage 2) under vacuum.

The invention relates to said method, the product obtained and pharmaceutical compositions which contain it.

The product obtained is characterised in that the polymer particles have a medicament concentration in their surface layers which is higher than that in their inner layers, the medicament being in the form of particles of nanometer dimensions.

DETAILED DESCRIPTION OF THE INVENTION

The characteristics and advantages of the method and product according to the invention will be more apparent from the following detailed description.

The method according to the invention is implemented in two stages as follows:

1st stage:

In the 1st stage the medicament is incorporated into a water-swellable but water-insoluble crosslinked polymer (or mixture of two or more such polymers) by any known method such as any of the following:

1a) the medicament is dissolved in a suitable solvent and a certain volume of the solution is sprayed onto a given quantity of polymer with the weight ratio of solution to polymer being chosen on the basis of the polymer swelling capacity and on the basis of the concentration of the medicament in the solution. The spraying ca be carried out in any apparatus used for the purpose, such as in a continuously stirred reactor, in a rotary evaporator under continuous rotation, in a vacuum granulator under constant mixing, in a mortar under light mixing with a pestle, or in a fluidised bed with the polymer kept suspended in an air stream. The product obtained is then dried in the aforesaid apparatuses or in other suitable apparatuses.

1b) the medicament is dissolved in a suitable solvent and a quantity of a water-swellable but water-insoluble crosslinked polymer (or a mixture of two or more such polymers ) is suspended in an excess of the solution obtained.

The suspension is kept stirred until the polymer particles swell. The suspension is then filtered or separated by other suitable means and the product is recovered and dried.

1c) the medicament in powder form and the water-swellable but water-insoluble crosslinked polymer (or mixture of two or more such polymers) in powder form are homogeneously mixed together and then ground together in a suitable apparatus such as a ball mill, high-energy vibratory mill, air jet mill etc.

1d) the medicament in powder form and the water-swellable but water-insoluble crosslinked. polymer in powder form are mixed homogeneously and then heated together to the medicament melting point in an apparatus such as an oven, rotary evaporator, reaction vessel, oil bath etc. until the medicament has melted and has been absorbed by the polymer.

The weight ratio of the medicament to said polymer (or mixture of two or more polymers) is in all cases between 0.1 and 1000 parts by weight of medicament per 100 parts by weight of polymer and preferably between 10 and 100 parts by weight of medicament per 100 parts by weight of polymer.

2nd stage:

In the 2nd stage the polymer in which the medicament has been incorporated by any of the methods described for the 1st stage is brought into contact with a solvent in the vapour or liquid state by any suitable method, for example by any of the following:

2a) the polymer with the medicament incorporated is introduced into a chamber into which the solvent in vapour form is fed through a valve. The chamber can be that in which the 1st stage was carried out;

2b) the polymer with the medicament incorporated is introduced into a sealed chamber already saturated with solvent vapour generated by a solvent container situated within the chamber and kept in the sealed chamber until saturation is complete;

2c) the polymer with the medicament incorporated is suspended in a fluidised bed by an air stream and is then sprayed with the liquid solvent or is exposed to an air stream saturated with the solvent vapour;

2d) the polymer with the medicament incorporated is suspended in an excess of solvent in liquid form, for example in a reaction vessel, in a mixer etc., and is then filtered off or separated by other means.

The time of contact between the polymer with the medicament incorporated and the solvent in vapour or liquid form is defined specifically for each medicament/polymer/solvent combination in order to obtain the desired characteristics of high medicament concentration in the surface layers and/or transformation of the physical state of the medicament into a crystalline state of lower melting point.

The treatment with solvent in gaseous form is conducted at a temperature preferably of between 20° and 100° C. and the treatment with solvent in liquid form is conducted at a temperature preferably of between 5° and 90° C.

The time of contact with the gaseous solvent is between 0.5 and 48 hours when the solvent is not the water, and between 12 and 36 hours when the solvent is the water. The time of contact with the liquid solvent is between 1 minute and 96 hours when the solvent is not the water, and between 1 and 15 hours when the solvent is the water. The final drying of the product is preferably conducted in an oven under vacuum at a temperature of between 20° and 100° C.

Examples of water-swellable but water-insoluble crosslinked polymers suitable for use (singly or in combinations of two or more than two) in the process of the invention are:

crosslinked polyvinylpyrrolidone (abbreviated to crospovidone) as described in National Formulary XV, Supplement 3, page 368;

crosslinked sodium carboxymethylcellulose as described in National Formulary XV, Supplement 3, page 367;

crosslinked β-cyclodextrin polymer as described in WO patent 83/00809 and by Fenyvest et al. in Pharmacie, 39, 473, 1984;

crosslinked dextran etc.

Of particular interest is the fact that the present invention has shown a new use for crosslinked β-cyclodextrin polymer, a substance which up to now has been used only as a disintegrator for solid pharmaceutical compositions and not as a support for medicaments.

However, according to the present invention, any polymer can be used which has the following characteristics:

hydrophilic polymer lattice allowing high swellability in water;

water insolubility deteroined by the nature of the polymer lattice.

The medicaments which can be used according to the present invention are preferably those which have limited water-solubility such as griseofulvin, indomethacin, diacerein, nicergoline, megestrol, progesterone, nifedipine, diltiazem, piroxicam, medroxyprogesterone acetate, clonidine, estradiol, etoposide, lorazepam and temazepam.

The solvent (or solvent mixtures) suitable for use in the method according to be invention are all those which are able to swell the polymer or to be absorbed by the polymer into which the medicament has been incorporated.

Examples of solvents are water, water-alcohol mixtures, methanol, ethanol, higher alcohols, acetone, chlorinated solvents, formamide, DMF, fluorinated hydrocarbons and others. The only limitation on the choice of solvent is that in the aforesaid case 2d), the solvent must have very limited dissolving power so that during treatment in the solvent, the quantity of medicament which is dissolved is limited.

One of the main characteristics of the product obtained by the method of the invention is that the particles have a medicament concentration in the surface layers which is higher than that of products obtained by the known art, is the medicament is preferentially localized in the surface layers of the particles instead of in their interior. This results in a higher medicament release rate, as the diffusion of the medicament molecules is much less hindered by the internal polymer lattice.

The high surface concentration of the medicament in the product of the present invention is demonstrated by X-ray photoelectronic spectroscopic analysis (XPS) which allows quantitative elementary investigation of the outer layers of the polymer as far as 100 Å from the surface.

A description of the XPS method is given in Kane P. F. et al., Characterization of Solid Surface, Plenum Press, New York 1978, pp 307–336.

This technique has been applied successfully to particles of crospovidone with incorporated medicament (F. Carli et al., J. Pharm. Sci., 963, 1985)

A hypothetical interpretation of the fact that a higher medicament concentration is obtained in the surface layers with the method of the invention is that this is determined mainly by the opening of the polymer lattice due to the solvent/polymer interaction when the polymer particles with incorporated medicament are treated with the solvent and also by the co-migration effect due to the solvent/medicament interaction during the final drying of the particles.

Another possible mechanism which can intervene in the preparation of the product according to the invention is that the physical state of the medicament can be trasformed from the strongly metastable amorphous state to a stable crystalline state having a much higher energy level than the original crystalline state of the pure medicament, as shown by the melting point being much lower than that of the pure medicament.

This high-energy crystalline state results in a high dissolving rate as in the case of the amorphous state, but has a much higher storage life than this latter.

The lower melting point of the medicament incorporated in the polymer according to the present invention can be attributed to the formation of very small crystals, in the nanometer range, within the polymer lattice. A theoretical explanation of this depressed melting point, based on the thermodynamic treatment of three-phase equilibria in systems of large surface area, has recently been proposed by F. Carli et al., Proceedings of the 13th Controlled Release Bioactive Material Symp., Norfolk, U.S.A., 1986; Proceedings of Ind. Pharm. Techn. Conference. London, 1988.

The reduction in melting point can be measured by DSC (differential scanning calorimetry) which also enables the residual crystallinity percentage to be determined by measuring the fusion energy in the sample.

The medicaments of this invention may be used for preparing capsules and tablets with controlled release, suspensions and transdermal films.

The following examples are given as non-limiting illustration of the invention.

EXAMPLE 1

1st stage:

10 g of crospovidone (Kollidon Cl, BASF) were swollen by slow addition of 20 ml of a 100 mg/ml solution of griseofulving in dimethylformamide, mixing the powder continuously in a mortar. The powder swollen in this manner was then placed in an oven under vacuum at a temperature of 100° C. for 12 hours, until it was completely dried.

2nd stage:

2 g of the product obtained in the first stage were disintegrated through a sieve (14 mesh) and then placed in a hermetically sealed container at ambient temperature, saturated with methylenechloride vapour from a receptacle filled with this solvent and placed in the container. After 24 hours the powder treated in this manner was dried for 1 hour at 30° C. in an oven under vacuum, sieved through a 14 mesh sieve and mixed for 10 minutes.

EXAMPLE 2

1st stage:

10 g of crospovidone (Knollidon Cl, BASF) were swollen by slow addition of 2 ml of a 100 mg/ml solution of griseofulvin in dimethylformamide, mixing the powder continuously in a mortar. The powder swollen in this manner was then placed in an oven under vacuum at a temperature of 100° C. for 12 hours, until it was completely dried.

2nd stage:

2 g of the powder with incorporated medicament obtained in the first stage were placed in a drier at ambient temperature and under an internal humidity of 90–92% obtained by an aqueous solution of suitable salts placed at the base of the same drier below the perforated floor on which the powder to be treated is placed. After 24 hours the powder treated in this manner was dried for 1 hour at 80° C. in an oven under vacuum, sieved through a 14 mesh sieve and mixed for 10 minutes.

EXAMPLE 3

1st stage:

10 g of crospovidone (Kollidon Cl, BASF) were swollen by slow addition of 20 ml of a 100 mg/ml solution of griseofulvin in dimethylformamide, mixing the powder continuously in a mortar. The powder swollen in this manner was then placed in an oven under vacuum at a temperature of 100° C. for 12 hours, until it was completely dried.

2nd stage:

1 g of the powder with incorporated medicament obtained in the first stage was wetted with 1 ml of demineralized water in a mortar, mixing the powder slowly for 1,5 hours. The swollen powder was dried for 1 hour at 80° C. in an oven under vacuum. It was then disintegrated through a 14 mesh sieve and mixed for 10 minutes.

EXAMPLE 4

1st stage:

500 g of crospovidone were swollen with 1000 ml of a 100 mg/ml solution of griseofulvin in dimethylformamide, this solution being added to the crospovidone kept mixing in a high-speed granulator. The swollen powder was then dried in an oven under vacuum at 100° C. for 12 hours and then disintegrated through a 14 mesh sieve and mixed for 10 minutes.

2nd stage:

100 g of the powder with incorporated medicament obtained in the first stage were suspended in a air-operated fluidised bed (GLATT) provided with a spraying apparatus (WURSTER) and sprayed with 200 ml of demineralized water in one hour. They were then dried while remaining suspended in the fluidised bed by the flow of hot air. The powder was then recovered in the collection sleeve, disintegrated through a 14 mesh sieve and mixed for 10 minutes.

EXAMPLE 5

1st stage:

3 g of griseofulvin were mixed with 9 g of crospovidone. One g of this mixture was placed in a rotary flask under vacuum (ROTOVAPOR) in an $N_2$ atmosphere (after evacuating the residual air) for 20 minutes under rotation while keeping the flask immersed in a silicone oil bath at 235° C. The flask was then cooled to ambient temperature, the powder extracted and sieved through a 14 mesh sieve and then mixed for 10 minutes.

2nd stage:

0.250 g of the powder with incorporated medicament obtained in the first stage were wetted in a mortar with 0.5 ml of demineralized water, mixing the system forcibly for 1,5 hours to homogeneously wet the powder. The wetted powder obtained was dried in an oven under vacuum at 80° C. for 1 hour, then disintegrated through a 14 mesh sieve and mixed for 10 minutes.

EXAMPLE 6

1st stage:

0.500 g of insoluble crosslinked β-cyclodextrin (CHINOIN) was swollen with 2 ml of a 50 mg/ml solution of griseofulvin in dimethylformamide. They were then placed in an oven under vacuum at 120° C. for three hours and then disintegrated through a 14 mesh sieve and mixed for 10 minutes.

2nd stage:

0.125 g of powdered crosslinked β-cyclodextrin with griseofulvin incorporated as in stage 1 was wetted with 1 ml of demineralized water by mixing slowly in a mortar for 1,5 hours. The powder treated in this manner was then placed in an oven under vacuum at 80° C. for 1 hour, sieved through a 14 mesh sieve and mixed for 10 minutes.

EXAMPLE 7

1st stage:

7.5 g of crosslinked sodium carboxymethylcellulose (Ac di Sol, FMC) and 2.5 g of indomethacin were sieved through a 14 mesh sieve and mixed for 10 minutes. The mixture obtained in this manner was placed in an oven under vacuum at 175° C. for 45 minutes and then disintegrated through a 14 mesh sieve and mixed for 10 minutes.

2nd stage:

0.25 g of crosslinked sodium carboxymethylcellulose with indomethacin incorporated as in stage 1 was wetted with 2 ml of demineralized water by mixing slowly in a mortar for one hour. The powder treated in this manner was then dried in an oven under vacuum at 80° C. for 1 hour, sieved through a 14 mesh sieve and mixed for 10 minutes.

EXAMPLE 8

1st stage:

10 g of crospovidone (Kollidon Cl, BASF) were swollen by slow addition of 20 ml of a 100 mg/ml solution of griseofulvin in dimethylformamide, mixing the powder continuously in a mortar. The powder swollen in this manner was then placed in an oven under vacuum at a temperature of 100° C. for 12 hours, untill it was completely dried.

2nd stage:

1 g of crospovidone with incorporated griseofulvin obtained in the first stage were suspended in 10 ml of demineralized water in a flask placed in a cupboard and shaken at ambient temperature for 6 hours.

The suspension was then filtered through a Whatman 42 filter and the powder retained on the filter was placed in an oven under vacuum for 1 hour at 80° C. The powder thus treated was disintegrated through a 14 mesh sieve and mixed for 10 minutes.

EXAMPLE 9

1st stage:

2.5 g of diacerein and 7.5 of crospovidone were sieved separately through a 14 mesh sieve and mixed for 10 minutes. They were then introduced together with the grinding means into the grinding chamber of a high-energy vibration ball mill and ground for 1 hour. They were then disintegrated through a 14 mesh sieve.

2nd stage:

8 g of the crospovidone powder with diacerein incorporated as in stage 1 were introduced into a hermetically sealed container saturated with methylenechloride vapour from a receptacle situated in said container and containing said solvent. After exposure to the vapour for 24 hours at ambient temperature the powder was dried in an oven under vacuum at ambient temperature for 2 hours and then disintegrated through a 14 mesh sieve and mixed.

EXAMPLE 10

1st stage:

1 g of crospovidone (Kollidon Cl, BASF) was swollen by slow addition of 1.7 ml of a 196 mg/ml solution of megestrol acetate methylenechloride while continuously mixing the powder in a mortar. The powder swollen in this manner was then left in an oven under vacuum at ambient temperature for two hours until it was completely dry.

2nd stage:

The powder obtained in the 1st stage was disintegrated through a sieve (No. 14 mesh) and then placed in a hermetically sealed container at ambient temperature, which was saturated with methylenechloride vapour from a receptacle containing said solvent and placed in the container. After 24 hours the treated powder was dried for 1 hour at 30° C. in an oven under vacuum, sieved through a 14 mesh sieve and mixed for 10 minutes.

EXAMPLE 11

1st stage:

1 g of crospovidone (Kollidon Cl, BASF) was swollen by 2 ml of a 100 mg/ml solution of nifedipine in methylenechloride while continuously mixing in a mortar. The powder swollen in this manner was then put in an oven under vacuum at 25° C. for 3 hours until it was completely dry.

2nd stage:

The powder obtained in the 1st stage was sieved through a 14 mesh sieve and then placed in a hermetically sealed container at 25° C. which was saturated with water vapour at a partial vapour pressure of 0.95, the vapour originating from water contained in a receptacle placed in the container. After 24 hours the treated powder was dried at 80° C. for 3 hours in an oven under vacuum, sieved through a 14 mesh sieve and mixed for 10 minutes.

EXAMPLE 12

1st stage:

0.95 g of crospovidone (Kollidon CL-M, BASF) were swollen by 2 ml a 95 mg/ml solution of nifedipine in methylenechloride while continuously mixing in a mortar. The swollen powder was then dried in an oven under vacuum at 30° C. for 3 hours until it was completely dry.

2nd stage:

The powder obtained in the 1st stage was sieved through a 14 mesh sieve and mixed and then placed in a hermetically sealed container at 25° C. which was saturated with methylenechloride vapour at a vapour pressure corresponding to the solvent temperature of 25° C. After 24 hours the treated powder was dried at 30° C. for 3 hours an oven under vacuum, sieved through a 14 mesh sieve and mixed for 10 minutes.

EXAMPLE 13

1st stage:

142 g of crospovidone (Kollidon CL-M, BASF) were swollen by 300 ml of a 95 mg/ml solution of nifedipine in methylenechloride; this solution was added to the crospovidone powder in the mixing chamber of a high speed granulator. The swollen powder was then dried in the same mixer at 30° C. and 400 mbar for 2 hours.

2nd stage:

The powder obtained in the let stage was further swollen in the same mixer with 250 ml of methylenechloride at 25° C. while mixing. At the end of the addition the mass was mixed for 24 hours in an environment saturated with the solvent. Subsequently the mass was dried at 30° C. and 400 mbar for 2 hours in the same mixer.

EXAMPLE 14

1st stage:

2 g of crospovidone (Kollidon CL-M, BASF) were swollen by 4 ml of a 20 mg/ml solution of nicergoline in methylenechloride while continuously mixing in a mortar. The swollen powder was then dried in an oven under vacuum at 30° C. for 3 hours until it was completely dry.

2nd stage:

The powder obtained in the 1st stage was sieved through a 14 mesh sieve and mixed and then placed in a hermetically sealed container at 25° C. which was saturated with methylenechloride vapour at a vapour pressure corresponding to the solvent temperature of 25° C. After 24 hours the treated powder was dried at 30° C. for 3 hours in an oven under vacuum, sieved through a 14 mesh sieve and mixed for 10 minutes.

To allow a comparison between the aforesaid examples implemented in accordance with the method of the present invention and the methods of the known art, the following examples A to G were conducted using known methods.

EXAMPLE A (comparison)

10 g of crospovidone were swollen with 20 ml of 100 mg/ml solution of griseofulvin in dimethylformamide, said solution being added slowly to the crospovidone powder which was kept under mixing in a mortar. The swollen powder was then dried in an oven under vacuum at a temperature of 100° C. for 12 hours and then disintegrated through a 14 mesh sieve and mixed for 10 minutes.

EXAMPLE B (comparison)

500 g of crospovidone were swollen with 1000 ml of a 100 mg/ml solution of griseofulvin in dimethylformamide, said solution being added to the crospovidone powder which was kept under mixing in the chamber of a high-speed granulator. The powder swollen in this manner was then dried in an oven under vacuum at 100° C. for 12 hours and then sieved through a 14 mesh sieve and mixed for 10 minutes.

EXAMPLE C (comparison)

3 g of griseofulvin and 9 g of crospovidone were sieved through a 14 mesh sieve and mixed for 10 minutes. 1 g of this mixture was placed in a rotary flask under vacuum containing $N_2$. The flask was immersed, under continuous rotation, in a silicone oil bath at 235° C. for 20 minutes and then cooled to ambient temperature. The crospovidone powder incorporated with griseofulvin was then disintegrated through a 14 mesh sieve and mixed for 10 minutes.

EXAMPLE D (comparison)

0.500 g of crosslinked β-cyclodextrin was swollen with 2 ml of a 50 mg/ml solution of griseofulvin in dimethylformamide, said solution being added slowly to the crosslinked β-cyclodextrin powder which was kept under mixing in a mortar. The swollen powder was then dried in an oven under vacuum at 120° C. for 3 hours and then disintegrated through a 14 mesh sieve and mixed for 10 minutes.

EXAMPLE E (comparison)

7.5 g of crosslinked sodium carboxymethylcellulose and 2.5 g of indomethacin were sieved through a 14 mesh sieve and mixed for 10 minutes. This mixture was placed in an oven under vacuum at 175° C. for 45 minutes and the powder thus obtained was then disintegrated through a 14 mesh sieve and mixed for 10 minutes.

EXAMPLE F (comparison)

2.5 of diacerein and 7.5 g of crospovidone were sieved through a 14 mesh sieve and then mixed for 10 minutes. The mixture was then introduced together with the grinding means into the grinding chamber of a high-energy vibration ball mill and ground for 1 hour. The powder obtained was then disintegrated through a 14 mesh sieve and mixed for 10 minutes.

EXAMPLE G (comparison)

1 g of crospovidone (Kollidon Cl, BASF) was placed in a mortar and swollen by slow addition of 1.7 ml of a 196 mg/ml solution of megestrol acetate in methylenechloride while continuously mixing. The swollen powder was then dried in an oven under vacuum at ambient temperature for 2 hours until it was completely dried and then disintegrated through a 14 mesh sieve and mixed for 10 minutes.

EXAMPLE H (comparison)

1 g of crospovidone (Kollidon Cl, BASF) was swollen by 2 ml of a 100 mg/ml solution of nifedipine in methylenechloride while continuously mixing the powder in a mortar.

The powder swollen in this manner was then placed in an oven under vacuum at 25° C. for 3 hours until it was completely dried, then sieved through a 14 mesh sieve and mixed.

Determination of the dissolving rate

The dissolving rate data for the products prepared by the method of this invention (Example 1–13) are given in Tables 1–9.

For comparison, each table also gives the dissolving rate data for the products prepared by known methods (Example A–H)

For all the medicaments studied, the method used was the U.S.P. XX No. 2 method using a SOTAX apparatus at 37° C. and a Beckman Du 65 spectrophotometer.

For the products containing griseofulvin 900 ml a pH 7.5 buffer solution were used while stirring at 150 r.p.m. The spectrophotometric reading of the suitably diluted samples was taken at 294 nm.

For the products containing indomethacin, 900 ml of a pH 6.8 buffer solution were used while stirring at 75 r.p.m. The spectrophotometric reading was taken at 319 nm.

For the products containing diacerein, 900 ml of a pH 5.5 buffer solution were used while stirring at 100 r.p.m. The spectrophotometric reading was taken at 255 nm.

For the products containing nifedipine, 900 ml of a pH 7.5 buffer solution were used while stirring at 150 r.p.m. The spectrophotometric reading was taken at 330 nm.

For the products containing megestrol acetate, 900 ml of a pH 5.2 buffer solution were used while stirring at 150 r.p.m.

For the determination of concentration, an HPLC of SPECTRA PHYSICS Mod. SP4A290/SP8800 was used, with mobile phase acetonitrile-water 50/50 v/v and flow rate 1 ml/min with a NOVAPAK $C_{18}$ colum and Mod. SP8490 UV detector, Imoz 292 nm.

As can be observed from the data of Tables 1–9, in the case of all the medicaments and swellable polymers used, the dissolving rate was clearly greater for the products prepared by the method of the invention than for the analogous products prepared by the previously known methods.

TABLE 1

Dissolving rate of products consisting of griseofulvin/crospovidone 1:5 w/w

| | Griseofulvin concentration (µg/ml) | | | |
|---|---|---|---|---|
| Time | Comparison preparation (Example A) | Preparation of invention (Example 1) | Preparation of invention (Example 2) | Preparation of invention (Example 3) |
| 5 min | 1.29 | 1.81 | 1.76 | 1.70 |
| 10 min | 1.53 | 2.55 | 2.25 | 2.67 |
| 15 min | 1.96 | 2.91 | 2.58 | 2.98 |
| 20 min | 2.41 | 3.42 | 2.86 | 3.31 |
| 30 min | 3.08 | 3.89 | 3.20 | 3.71 |
| 40 min | 3.38 | 4.24 | 3.85 | 3.85 |
| 60 min | 3.52 | 4.59 | 3.81 | 4.05 |

N.B. The values reported are the mean of at least three repeats; maximum C.V. ≦8%

TABLE 2

Dissolving rate of products consisting of griseofulving/crospovidone 1:5 w/w

Griseofulvin concentration (µg/ml)

| Time | Comparison preparation (Example B) | Preparation of invention (Example 4) |
|---|---|---|
| 5 min | 0.87 | 1.39 |
| 10 min | 1.25 | 1.86 |
| 15 min | 1.81 | 2.20 |
| 20 min | 2.07 | 2.43 |
| 30 min | 2.57 | 2.83 |
| 40 min | 2.73 | 2.98 |
| 60 min | 3.14 | 3.30 |

N.B. The values reported are the mean of at least three repeats; maximum C.V. ≦10%

TABLE 3

Dissolving rate of products consisting of griseofulving/crospovidone 1:3 w/w.

Griseofulvin concentration (µg/ml)

| Time | Comparison preparation (Example C) | Preparation of invention (Example 5) |
|---|---|---|
| 5 min | 1.99 | 2.10 |
| 10 min | 2.88 | 3.30 |
| 15 min | 3.21 | 3.75 |
| 20 min | 3.63 | 3.96 |
| 30 min | 3.87 | 4.32 |
| 40 min | 4.13 | 4.52 |
| 60 min | 4.46 | 4.57 |

N.B. The values reported are the mean of at least three repeats; maximum C.V. ≦9%

TABLE 4

Dissolving rate of products consisting of griseofulvin/crosslinked β-cyclodextrin 1:5 w/w Griseofulvin concentration (µg/ml)

| Time | Comparison preparation (Example D) | Preparation of invention (Example 6) |
|---|---|---|
| 5 min | 0.99 | 1.47 |
| 10 min | 1.56 | 2.33 |
| 15 min | 2.25 | 2.85 |
| 20 min | 2.25 | 3.05 |
| 30 min | 3.10 | 3.56 |
| 40 min | 3.36 | 4.04 |
| 60 min | 3.70 | 4.56 |

N.B. The values reported are the mean of at least three repeats; maximum C.V. ≦9%

TABLE 5

Dissolving rate of products consisting of indomethacin/ crosslinked sodiumcarboxymethylcellulose 1:3 w/w Indomethacin concentration (µg/ml)

| Time | Comparison preparation (Example E) | Preparation of invention (Example 7) |
|---|---|---|
| 5 min | 4.77 | 7.98 |
| 10 min | 6.43 | 9.27 |

TABLE 5-continued

Dissolving rate of products consisting of indomethacin/ crosslinked sodiumcarboxymethylcellulose 1:3 w/w Indomethacin concentration (µg/ml)

| Time | Comparison preparation (Example E) | Preparation of invention (Example 7) |
|---|---|---|
| 15 min | 8.23 | 9.78 |
| 20 min | 9.34 | 9.68 |

N.B. The values reported are the mean of at least three repeats; maximum C.V. ≦7%

TABLE 6

Dissolving rate of products consisting of griseofulving/crospovidone 1:5 w/w

Griseofulvin concentration (µg/ml)

| Time | Comparison preparation (Example A) | Preparation of invention (Example 8) |
|---|---|---|
| 5 min | 1.29 | 1.75 |
| 10 min | 1.59 | 2.59 |
| 15 min | 1.96 | 3.04 |
| 20 min | 2.41 | 3.21 |
| 30 min | 3.08 | 3.63 |
| 40 min | 3.38 | 3.83 |
| 60 min | 3.52 | 4.27 |

N.B. The values reported are the mean of at least three repeats; maximum C.V. ≦8%

TABLE 7

Dissolving rate of products consisting of diacerein/crospovidone 1:3 w/w.

Diacerein concentration (µg/ml)

| Time | Comparison preparation (Example F) | Preparation of invention (Example 9) |
|---|---|---|
| 1 min | 9.78 | 9.08 |
| 3 min | 13.64 | 16.55 |
| 5 min | 15.27 | 19.86 |
| 10 min | 17.08 | 23.00 |
| 15 min | 18.26 | 24.97 |
| 30 min | 19.47 | 26.26 |
| 45 min | 21.95 | 26.25 |
| 60 min | 23.01 | 26.30 |

TABLE 8

Dissolving rate of products consisting of megestrol acetate/crospovidone 1:3 w/w.

Megestrol acetate concentration (µg/ml)

| Time | Comparison preparation (Example G) | Preparation of invention (Example 10) |
|---|---|---|
| 10 min | 0.0239 | 0.0397 |
| 20 min | 0.0438 | 0.0628 |
| 30 min | 0.0714 | 0.0934 |
| 45 min | 0.0891 | 0.1160 |
| 60 min | 0.1091 | 0.1382 |
| 90 min | 0.1610 | 0.1766 |
| 120 min | 0.1838 | 0.1927 |

TABLE 9

Dissolving rate of products consisting of nifedipine/crospovidone 1:3 w/w.

Nifedipine concentration (µg/ml).

| Time | Comparison preparation (Example H) | Preparation of invention (Example 11) | Preparation of invention (Example 12) | Preparation of invention (Example 13) |
| --- | --- | --- | --- | --- |
| 5 min | 1.78 | 1.82 | 3.71 | 4.03 |
| 10 min | 2.44 | 2.12 | 4.22 | 4.39 |
| 15 min | 2.80 | 2.54 | 4.46 | 4.23 |
| 30 min | 3.54 | 3.20 | 4.69 | 4.47 |
| 60 min | 4.15 | 4.26 | 4.82 | 4.73 |
| 90 min | 4.56 | 4.70 | 5.03 | 4.91 |

Differential scanning calorimetry data

A further characteristic of the products prepared by the method of the present invention is that they have a high-energy crystalline state, ie they have a melting point which is lower than that of the medicament as such. This lowering of melting point is due to the formation of very fine crystals in the manometer dimensional range (so-called manocrystals).

Table 10 shows the thermoanalytical data relative to the products prepared according to the invention, the data being obtained using a differential scanning calorimeter TA 3000 of Mettler (Switzerland) with nitrogen flow and a heating rate of 10° K. min$^{-1}$. For comparison purposes Table 10 also shows data relative to products prepared by the conventional method, whereas Table 11 shows the thermoanalytical characteristics of the crystalline active principles as such.

Comparing the data for products prepared in accordance with the invention with those for the products prepared by conventional methods and those of the active principles as such, it can be seen that in every case the activation by treatment with solvent leads to polymer products containing incorporated medicament crystals having melting point clearly less than that of the medicaments as such. In contrast, the conventional preparation method produces products having the same melting point as the medicaments as such.

In this respect, for the griseofulvin/crospovidone products there is a melting point reduction of 13°–30° C.; for the nifedipine/crospovidone products there is a reduction of the order of 20° C.; and for the diacerein/crospovidone products there is a melting point reduction of 40°–50° C.

As stated, these melting point reductions indicate that the medicaments are in a crystalline state of higher energy than that of the medicaments as such, with consequent solubility increase. In addition, it has also already been stated that these melting point reductions are due to extremely fine crystal dimensions of nanometer level. Consequently the products activated by the method of the invention have improved bioavailability characteristics compared with the medicaments as such and with the products prepared by the conventional method.

TABLE 10

Differential scanning calorimetry data for the medicament/swellable insoluble polymer products prepared by the method of the invention and by the traditional method.

| | THERMAL CHARACTERISTICS | MELTING POINT | HEAT OF FUSION |
| --- | --- | --- | --- |
| Example A[a] | 1 PEAK ONLY | 219.0° C. | 7.8 J/g |
| Example B[a] | 1 PEAK ONLY | 220.3° C. | 19.2 J/g |
| Example 1[b] | 1 PEAK ONLY | 194.2° C. | 44.2 J/g |
| Griseofulvin/crospovidone systems 1/5 w/w: | | | |
| Example 2[b] | 2 PEAKS | 191.7° C. | 30.3 J/g |
| | | 220.2° C. | 6.6 J/g |
| Example 3[b] | 2 PEAKS | 196.8° | 107.3 J/g |
| Example 4[b] | 2 PEAKS | 198.8° | 45.6 J/g |
| | | 220.8° C. | 8.8 J/g |
| Griseofulvin/crospovidone systems 1/3 w/w: | | | |
| Example C[a] | NO PEAK | — | — |
| Example 5[b] | 1 PEAK ONLY | 207.0° C. | 78.6 J/g |
| Nifedipine/crospovidone systems 1/5 w/w: | | | |
| Example H[a] | NO PEAK | — | — |
| Example 11[b] | 1 PEAK ONLY | 154.3° C. | 41.4 J/G |
| Example 12b | NO PEAK | — | — |
| Example 13b | NO PEAK | — | — |
| Diacerein/crospovidone systems 1/3 w/w: | | | |
| Example F[a] | NO PEAK | — | — |
| Example 9[b] | 2 PEAKS | 176.0° C. | 25.7 J/g |
| | | 202.7° C. | 14.4 J/g |

[a] products prepared by the traditional method
[b] products prepared by the method of the invention

TABLE 11

Differential scanning calorimetry data for active principles as such.

| ACTIVE PRINCIPLE | THERMAL CHARACTERISTICS | MELTING POINT | HEAT OF FUSION |
| --- | --- | --- | --- |
| Griseofulvin | 1 PEAK ONLY | 219.8° C. | 120.4 J/g |
| Nifedipine | 1 PEAK ONLY | 172.8° C. | 110.3 J/g |
| Diacerein | 1 PEAK ONLY | 251.3° C. | 229.3 J/g |

X-ray photoelectronic spectroscopy (XPS) data

The XPS data for some of the aforesaid examples of the method according to the invention are given in Table 12. The data are presented as suggested in J. Pharm. Sci., 1986, ie as ratio of the surface concentrations (or emission peak intensity) of two atoms present in the medicament structure and polymer structure respectively.

The more this ratio is in favour of the atom present in the medicament structure, the higher the medicament concentration on the surface of the polymer particles.

The values found for each product prepared in accordance with the invention indicate a medicament concentration in the polymer surface layers which is clearly higher than that found for the same product prepared by known methods.

More specifically, for the griseofulvin/crospovidone products, the Cl/N ratio (Cl=intensity of chlorine emission peak; N= intensity of nitrogen peak) is higher for products prepared as indicated in Example 2 of the method of the present invention than for the same products prepared by known methods (Example A).

As the chlorine atom is present only in the griseofulvin structure, these data indicate a surface griseofulvin concentration which is clearly higher for the products prepared in accordance with the invention.

In the case of the nifedipine/crospovidone products, the ratio used for evaluating the surface nifedipine concentration is O/N where O is the intensity of the oxygen atom peak and N is the nitrogen peak. Again in this case, as Table 12 shows, the products prepared in accordance with Example 11 of the present invention have a surface nifedipine concentration which is clearly higher than the products prepared by known methods (Example H).

In this respect, there is much more surface oxygen in the case of Example 11, and the oxygen is a distinctly heavier atomic species in the nifedipine structure than in the crospovidone polymer structure.

TABLE 12

X-ray photoelectronic spectroscopy data for the swellable insoluble medicament/polymer products prepared by the method of the invention and by the conventional method

| Product | Example | |
|---|---|---|
| | | Cl/N (ratio of chlorine peak to nitrogen peak) |
| Griseofulvin/crospovidone 1/5 w/w | Example A[a] Example 2[b] | 0.043 0.242 |
| | | O/N (ratio of oxygen peak to nitrogen peak) |
| Nifedipine/crospovidone 1/5 w/w | Example H[a] Example 11[b] | 1.64 1.96 |

[a] products prepared by traditional method
[b] products prepared in accordance with invention.

I claim:

1. A poorly soluble medicament supported on a polymer substance in a form capable of increasing the dissolving rate of said medicament, prepared by a method comprising:

1) bringing a medicament incorporated into particles of a crosslinked polymer which is swellable in water but insoluble in water by treating said polymer particles with a solution of said medicament in a non-aqueous organic solvent and drying, or by mixing said polymer particles with said medicament, heating to the medicament melting point, and then cooling at ambient temperature;

2) bringing the thus formed product into contact with a non-aqueous organic solvent, in gaseous or liquid form, which is capable of swelling said polymer, wherein said contact with said gaseous solvent is conducted for a period of time of between 0.5 and 48 hours, and wherein said contact with said non-aqueous organic liquid solvent is conducted for a period of time of between 1 minute and 96 hours; and 3) drying the product obtained in step 2) under vacuum to produce a medicament supported on a polymer substance wherein said medicament has been transformed from a metastable amorphous state to a stable high-energy crystalline state and is present in higher concentration in the surface layers of said polymer particles than in their inner layers.

2. A capsule, controlled-release tablet, suspension, or transdermal film, comprising a medicament prepared according to the method of claim 1.

3. A poorly soluble medicament prepared according to claim 1 wherein said medicament is supported on a polymer substance in a form capable of increasing the dissolving rate of said medicament, and wherein the medicament concentration is higher in the surface layers of the polymer particles than in their inner layers.

4. A poorly soluble medicament prepared according to claim 1 wherein said medicament is supported on a polymer substance in a form capable of increasing the dissolving rate of said medicament, and wherein said medicament is in the form of particles of nanometer dimensions.

5. The poorly soluble medicament supported on a polymer substance in a form capable of increasing the dissolving rate of said medicament of claim 1, wherein said polymer is selected from the group consisting of crosslinked polyvinylpyrrolidone, crosslinked sodium carboxymethylcellulose, crosslinked β-cyclodextrin polymer, and crosslinked dextran, and wherein said medicament is selected from the group consisting of griseofulvin, indomethacin, diacerein, megestrol, and nicergoline.

* * * * *

UNITED STATES PATENT AND TRADEMARK OFFICE
CERTIFICATE OF CORRECTION

PATENT NO. : 5,569,469
DATED : Oct. 29, 1996
INVENTOR(S) : Lovrecich

It is certified that error appears in the above-indentified patent and that said Letters Patent is hereby corrected as shown below:

On the title page, page insert the following item:

-- [30]    Foreign Application Priority Data

Oct. 17, 1988  [IT]  Italy .....................22336 A/88 --.

Signed and Sealed this

Twenty-seventh Day of May, 1997

Attest:

BRUCE LEHMAN

Attesting Officer         Commissioner of Patents and Trademarks